(12) United States Patent
Mayer et al.

(10) Patent No.: US 8,802,568 B2
(45) Date of Patent: Aug. 12, 2014

(54) METHOD FOR MANUFACTURING CHEMICAL SENSOR WITH MULTIPLE SENSOR CELLS

(71) Applicant: Sensirion AG, Stafa (CH)

(72) Inventors: Felix Mayer, Stafa (CH); Markus Graf, Zurich (CH); Lukas Burgi, Zurich (CH)

(73) Assignee: Sensirion AG, Stafa (CH)

( * ) Notice: Subject to any disclaimer, the term of this patent is extended or adjusted under 35 U.S.C. 154(b) by 0 days.

(21) Appl. No.: 13/628,719

(22) Filed: Sep. 27, 2012

(65) Prior Publication Data

US 2014/0084390 A1    Mar. 27, 2014

(51) Int. Cl.
- *H01L 21/302* (2006.01)
- *H01L 21/461* (2006.01)
- *H01L 21/00* (2006.01)
- *H01L 21/4763* (2006.01)

(52) U.S. Cl.
USPC ............... 438/689; 438/48; 438/49; 438/633; 438/691

(58) Field of Classification Search
USPC ............... 438/48, 49, 633, 689, 691
See application file for complete search history.

(56) References Cited

U.S. PATENT DOCUMENTS

| | | | |
|---|---|---|---|
| 5,345,213 A | 9/1994 | Semancik et al. | |
| 5,891,398 A | 4/1999 | Lewis et al. | |
| 5,907,765 A | 5/1999 | Lescouzeres et al. | |
| 6,103,033 A | 8/2000 | Say et al. | |
| 6,325,979 B1 | 12/2001 | Hahn et al. | |
| 6,753,144 B1 | 6/2004 | Hirota et al. | |
| 6,767,396 B2 | 7/2004 | McElligott et al. | |
| 6,939,451 B2 | 9/2005 | Zhao et al. | |
| 7,061,061 B2 | 6/2006 | Goodman et al. | |
| 7,096,716 B2 | 8/2006 | Theil | |
| 7,115,354 B2* | 10/2006 | Hatakeyama et al. | 430/322 |
| 7,225,535 B2 | 6/2007 | Feldman et al. | |
| 7,442,502 B2 | 10/2008 | Hirota et al. | |
| 7,495,300 B2 | 2/2009 | Gardner et al. | |
| 7,721,412 B2 | 5/2010 | Say et al. | |
| 7,771,620 B2 | 8/2010 | Chung et al. | |
| 7,797,814 B2 | 9/2010 | Say et al. | |
| 7,824,539 B2 | 11/2010 | Zhou et al. | |
| 7,911,010 B2 | 3/2011 | Stetter | |

(Continued)

FOREIGN PATENT DOCUMENTS

| | | |
|---|---|---|
| CN | 101363810 | 2/2009 |
| CN | 101549858 | 10/2009 |

(Continued)

OTHER PUBLICATIONS

A. Hierlemann, "CMOS-based Chemical Sensors," Advanced Micro and Nanosystems, vol. 2, CMOS-MEMS, 335-390.

(Continued)

*Primary Examiner* — Matthew Reames
*Assistant Examiner* — Dilinh Nguyen
(74) *Attorney, Agent, or Firm* — Cooper & Dunham LLP

(57) ABSTRACT

In a method for manufacturing a chemical sensor with multiple sensor cells, a substrate is provided and an expansion inhibitor is applied to the substrate for preventing a sensitive material to be applied to an area on the substrate for building a sensitive film of a sensor cell to expand from said area. The sensitive material is provided and the sensitive film is built by contactless dispensing the sensitive material to said area.

21 Claims, 4 Drawing Sheets

(56) References Cited

U.S. PATENT DOCUMENTS

| | | | |
|---|---|---|---|
| 2004/0023253 A1 | 2/2004 | Kunwar et al. | |
| 2005/0051511 A1 | 3/2005 | Ke et al. | |
| 2006/0014005 A1 | 1/2006 | Basco et al. | |
| 2006/0034731 A1 | 2/2006 | Lewis et al. | |
| 2006/0055502 A1 | 3/2006 | Usui | |
| 2006/0183261 A1 | 8/2006 | Dudenhoefer et al. | |
| 2006/0272942 A1 | 12/2006 | Sirringhaus | |
| 2007/0095662 A1 | 5/2007 | Suzuki | |
| 2008/0035478 A1 | 2/2008 | Wegner et al. | |
| 2008/0087542 A1 | 4/2008 | Moore et al. | |
| 2008/0217173 A1 | 9/2008 | Varney et al. | |
| 2009/0153942 A1* | 6/2009 | Daniel et al. | 359/296 |
| 2009/0211639 A1* | 8/2009 | Park et al. | 136/262 |
| 2009/0242405 A1* | 10/2009 | Mayer et al. | 204/435 |
| 2009/0249621 A1 | 10/2009 | Rochat et al. | |
| 2010/0021659 A1 | 1/2010 | Feldman et al. | |
| 2010/0035245 A1 | 2/2010 | Stiene et al. | |
| 2010/0055729 A1 | 3/2010 | Ahn | |
| 2010/0060465 A1 | 3/2010 | Stetter | |
| 2010/0132788 A1 | 6/2010 | Petrat et al. | |
| 2010/0140673 A1 | 6/2010 | Daniel et al. | |
| 2010/0143675 A1 | 6/2010 | Guckian et al. | |
| 2010/0170793 A1 | 7/2010 | Feldman et al. | |
| 2011/0042211 A1 | 2/2011 | Huang et al. | |
| 2011/0171363 A1 | 7/2011 | Komatsu et al. | |
| 2011/0174799 A1 | 7/2011 | Ali et al. | |
| 2011/0233472 A1 | 9/2011 | Hotz et al. | |
| 2012/0050038 A1 | 3/2012 | Stetter | |
| 2012/0138871 A1 | 6/2012 | Dorfman et al. | |

FOREIGN PATENT DOCUMENTS

| | | |
|---|---|---|
| DE | 19642453 | 10/1996 |
| DE | 10119405 | 4/2001 |
| DE | 102005040055 | 3/2006 |
| DE | 102006019534 | 11/2007 |
| DE | 102008064331 | 12/2008 |
| DE | 102009031773 | 6/2009 |
| DE | 102010017844 | 4/2010 |
| EP | 1308705 | 5/2007 |
| EP | 1933138 | 6/2008 |
| GB | 2464016 | 7/2010 |
| JP | 2004205294 | 7/2004 |
| JP | 2011033592 | 2/2011 |
| KR | 100843169 | 7/2008 |
| KR | 100845717 | 7/2008 |
| KR | 20110098423 | 9/2011 |
| WO | 2007124725 | 11/2007 |
| WO | 2008126897 | 10/2008 |

OTHER PUBLICATIONS

Applied Sensor, "Metal Oxide Semiconductor (MOS) Sensors", www.appliedsensors.com, 2 pages.

Nanoparticle Dispersions & Suspensions, "Dispersions, Suspensions & Inks", Oct. 23, 2012, 1 page.

Ralph Eichler, "President's Selection, ETHZ, Nanotropfchenweise and the Translations Article", "Nano Drop by Drop", Nov. 2011, 3 pages.

J. Puigcorbe et al., "High Temperature Degradation of Pt/Ti Electrodes in Micro-Hotplate Gas Sensors", Institute of Physics Publishing, 13 (2003), S119-S124.

I. Simon et al., "Micromachined Metal Oxide Gas Sensors: Opportunities to Improve Sensor Performance," Science B.V., Sensors and Acuators, B 73 (2001), 1-26.

Martin Heule et al., "Miniaturised Arrays of Tin Oxide Gas Sensors on Single Microhotplate Substrates Fabricated by Micromolding in Capillaries", Elsevier Science B.V., Sensors and Acuators B 93 (2003), 100-106.

A. Friedberger et al., "Micromechanical Fabrication of Robust Low-Power Metal Oxide Gas Sensors," Sensors and Acuators B 93 (2003), 345-349.

Markus Graf et al., "CMOS Monolithic Metal-Oxide Sensor System Comprising a Microhotplate and Associated Circuitry", IEEE Sensors Journal, vol. 4, No. 1, Feb. 2004, pp. 9-16.

Hey-Jin Lim et al., "Gas Sensing Properties of ZnO Thin Films Prepared by Microcontact Printing", Sensors and Actuators A 125, 2006, pp. 405-410.

B. Ruhland et al., "Gas-Kinetic Interactions of Nitrous Oxides with $SnO_2$, Surfaces", Sensors and Actuators B 50, 1998, pp. 85-94.

Wenfeng Shen, "Properties of $SnO_2$ Based Gas-Sensing Thin Films Prepared by Ink-Jet Printing", Sensors and Actuators B 166-167, 2012, pp. 110-116.

Copy of European Search Report No. 13004568.5, completed on Jan. 27, 2014.

* cited by examiner

METHOD FOR MANUFACTURING CHEMICAL SENSOR WITH MULTIPLE SENSOR CELLS

BACKGROUND OF THE INVENTION

The invention relates to a chemical sensor and to a method for manufacturing a chemical sensor.

A chemical sensor performs a detection of chemical substances or compounds which are also denoted as analytes contained in a gas, or possibly in a fluid, supplied to the chemical sensor.

In case multiple different analytes shall be detected by a chemical sensor, the chemical sensor may comprise multiple sensor cells with each sensor cell being designed for detecting one or more of the subject analytes.

BRIEF SUMMARY OF THE INVENTION

According to a first aspect of the present invention, a method for manufacturing a chemical sensor with multiple sensor cells is provided. According to this method, a substrate is provided and an expansion inhibitor is applied to the substrate for preventing a sensitive material to be applied to an area on the substrate for building a sensitive film of a sensor cell to expand from said area. The sensitive material is provided and the sensitive film is built by contactless dispensing the sensitive material to said area.

Preferred embodiments of the method may contain one or more of the following features:
the sensitive material is dispensed in a liquid phase to said area;
applying the expansion inhibitor includes applying a barrier at edges of said area for preventing the sensitive material to be applied to said area to escape from said area;
the barrier includes a rim protruding from the substrate around said area;
the barrier includes a recess in the substrate around said area;
applying the expansion inhibitor includes treating a surface of the substrate for providing a first surface energy in said area, and for providing a second surface energy outside said area, which second surface energy is less than the first surface energy, for making said area a preferred zone for the sensitive material to wet to;
the surface of the substrate provides the first surface energy, and outside said area the surface of the substrate is covered by a coating providing the second surface energy;
the surface of the substrate provides the second surface energy, and in said area the surface of the substrate is covered by a coating providing the first surface energy;
applying the expansion inhibitor includes applying an adhesion film to said area for making the sensitive material to be applied to said area adhere to the adhesion film;
applying expansion inhibitors to the substrate to prevent the sensitive material to be applied to multiple areas on the substrate for building sensitive films of the multiple sensor cells to expand from said multiple areas, and building the sensitive films by contactless dispensing of the sensitive material to said multiple areas;
at least two neighbouring areas of said multiple areas share a common component of the expansion inhibitors assigned to said at least two neighbouring areas;
the common component includes a common barrier applied between said at least two neighbouring areas for preventing the sensitive material dispensed to a first of said at least two neighbouring areas to escape into a second of said at least two neighbouring areas, and for preventing the sensitive material dispensed to the second of said at least two neighbouring areas to escape into the first of said at least two neighbouring areas;
the sensitive material is jet dispensed to said area on the substrate;
a defined portion of the sensitive material is jet dispensed to said area on the substrate;
the sensitive material is ink jet printed to said area on the substrate;
the sensitive material is ink jet printed to multiple areas on the substrate simultaneously, and preferably is ink jet printed to all areas on the substrate simultaneously;
the sensitive material is ink jet printed to said multiple areas on the substrate simultaneously through multiple nozzles of a print head;
the sensitive material is applied to a first of said multiple areas in a first composition through a first nozzle of a print head, and is applied to a second of said multiple areas in a second composition through a second nozzle of the print head;
the sensitive material in the first composition and the sensitive material in the second composition is applied simultaneously through the first and the second nozzle respectively;
the sensitive material comprises metal oxide nano-particles;
the sensitive material comprises polymer material;
applying the expansion inhibitor includes applying an electrode pattern to the substrate, and in particular applying an electrode pattern to the substrate that confines said area;
the chemical sensor is a chemoresistive sensor containing a metal-oxide semiconductor material;
the substrate has a first thickness in a first region and a second thickness in a second region wherein the first thickness is smaller than the second thickness, and said area is arranged in the first region such that said sensitive material is dispensed in said first region.

According to a further aspect of the present invention, a method for manufacturing multiple chemical sensors with multiple sensor cells is provided. According to this method, a wafer is provided and expansion inhibitors are applied to the wafer for preventing a sensitive material to be applied to multiple areas on the wafer for building sensitive films of the multiple sensor cells for the chemical sensors to expand from said multiple areas. The sensitive material is provided and the sensitive films are built by contactless dispensing the sensitive material to said multiple areas. The wafer is separated into the chemical sensors.

According to another aspect of the present invention, a chemical sensor with multiple sensor cells is provided. The chemical sensor comprises a substrate. Each sensor cell of the multiple sensor cells comprises a sensitive film built from a sensitive material and covering an area on the substrate, and an expansion inhibitor for preventing the sensitive material to expand from said area when being applied thereto.

In a preferred embodiment of the chemical sensor, the area covered by the sensitive film is dimensioned at less than 50 µm times 50 µm. In another preferred embodiment of the chemical sensor, the substrate has a first region with a first thickness and a second region with a second thickness exceeding the first thickness, wherein the area covered by the sensitive film is arranged in the first region. In another preferred embodiment, electronic circuitry is integrated into the substrate.

Other advantageous embodiments are listed in the dependent claims as well as in the description below.

The described embodiments similarly pertain to the sensor and the method. Synergetic effects may arise from different combinations of the embodiments although they might not be described in detail.

BRIEF DESCRIPTION OF THE DRAWINGS

The embodiments defined above and further aspects, features and advantages of the present invention can also be derived from the examples of embodiments to be described hereinafter and are explained with reference to the drawings. In the drawings it is illustrated in.

DETAILED DESCRIPTION OF THE INVENTION

Figure 1:
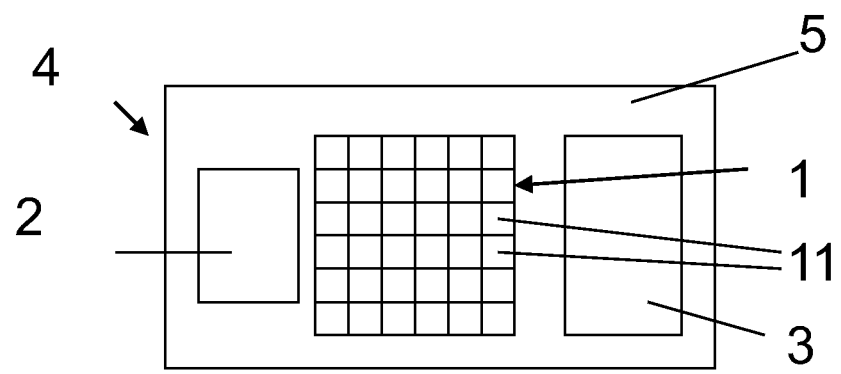
FIG. 1 a top view on a schematic sensor chip according to an embodiment of the present invention, FIG. 2 a top view on a chemical sensor of the sensor chip according to FIG. 1, and below a cut along lines A-A', FIG. 3 a top view on a chemical sensor according to another embodiment of the present invention, and below a cut along lines A-A', FIG. 4 a schematic cut illustrating the manufacturing of a chemical sensor according to an embodiment of the present invention, FIG. 5 a schematic cut illustrating the manufacturing of a chemical sensor according to another embodiment of the present invention, FIG. 6 a top view on a chemical sensor according to another embodiment of the present invention, and below a cut along lines A-A', FIG. 7 a top view on a section of a wafer comprising chemical sensors according to an embodiment of the present invention, FIG. 8 a cut of the chemical sensor section of the sensor chip of FIG. 1, FIG. 9 a more detailed cut view of a sensor cell of the sensor of FIG. 6, and FIG. 10 a top view on three different designs of a sensor cell of a chemical sensor according to another embodiment of the present invention.

A chemical sensor may in one embodiment of the present invention comprise at least one sensitive film made from material being sensitive to one or more analytes. The chemical sensor preferably is embodied as a sensor array comprising a set of sensor cells, wherein each sensor cell may include such a sensitive film. A sensor cell may be understood as an entity of the chemical sensor which may be read individually. Preferably, in the embodiment of the sensor array, each or at least some of the sensitive films are sensitive to different analytes. These sensitive films may accordingly be built from sensitive material of different composition. The corresponding sensitive films may exhibit different sensitivities from cell to cell such that each cell of the sensor array may be mainly sensitive to a specific analyte and as such may allow detecting the presence or absence or concentration of such analyte. "Mainly" in this context shall mean, that a sensor cell is more sensitive to the subject analyte than to other analytes. Preferably, in such array of sensor cells the sensitive films do not touch each other. The chemical sensor performs a detection of chemical substances or compounds—collectively denoted as analytes—contained in a gas, or possibly in a fluid supplied to the chemical sensor. Such analytes may include one or more of, for example, CO2, NOX, ethanol, CO, ozone, ammonia, formaldehyde, or xylene without limitation.

The chemical sensor may comprise a sensitive material, e.g. in form of a film, the analyte may interact with. As a result, an electrical property of the sensor material may be modified upon interaction such as its electrical conductance, which principle preferably is applied in metal oxide chemical sensors, or an optical property of the sensor material may be modified such as its transmission rate, for example. Then, the electrical or optical property of a combination of the analyte and the sensor material is measured and allows a conclusion as to the analyte, such as by way of comparison to a property of the sensor material measured without the presence of the analyte.

Specifically, the sensitive film/s may contain a metal oxide material, and in particular a semiconducting metal oxide material, and specifically may contain metal oxide materials of different composition per sensitive film. Such metal oxide material generally may include one or more of tin oxide, zinc oxide, titanium oxide, tungsten oxide, indium oxide and gallium oxide. Such metal oxides may be used for the detection of analytes such as VOCs, carbon monoxide, nitrogen dioxide, methane, ammonia or hydrogen sulphide. Metal oxide sensors are based on the concept that gaseous analytes interact with the metal oxide layer at elevated temperatures of the sensitive layer in the range of more than 100° Celsius, and specifically between 250° C. and 350° Celsius. As a result of the catalytic reaction, the conductivity of the sensitive film may change which change can be measured. Hence, such chemical sensors are also denoted as high temperature chemoresistors for the reason that a chemical property of the analyte is converted into an electrical resistance at high temperatures of the sensitive film. In a metal oxide chemical sensor with multiple sensor cells, all sensitive films may be heated by a common heater, or each sensitive film may be heated by an individual heater.

However, the chemical sensor may alternatively be based on one of the following measurement principles without limitation: A chemomechanical principle, in which a mass change upon absorption is transformed into a surface acoustic wave, or into a shift of a frequency of a cantilever resonance, for example. Alternatively, there may be thermal sensing concepts applied, e.g. by making use of pellistors which may serve as a catalytic thermal sensor in which heat is generated or consumed during combustion. Alternatively, the chemical sensor may rely on optical detection, such as in form of a microspectrometer, or an NDIR, or may make use of electrochemical reactions such as being enabled by solid state electrolytes in combination with voltammetric, potentiometric, or conductometric measurement principles. In another embodiment, a binding energy of an analyte can be determined and allows for a derivation as to the presence of the analyte.

Preferably, by means of such chemical sensor a gas may be investigated at least as to the absence or presence of the subject analytes the chemical sensor is sensitive to. Hence, the gas supplied to the chemical sensor may be analyzed by means of the chemical sensor as to if and which of the chemical substances or compounds the chemical sensor is sensitive to are present in the gas supplied. A combination of analytes detected in the gas supplied may suggest for a certain odour or for a certain gas. It is always subject to a design of the chemical sensor as to how many different analytes and/or how many different properties of an analyte the chemical sensor is sensitive to. It is noted that for the different analytes the chemical sensor is sensitive to it is not required to always measure the same property per analyte. Different properties may be measured for different analytes.

In the context of the present invention, a substrate shall include any platform for dispensing a suspension or solution of sensitive material to. The substrate may be one of a semiconductor, a glass or a ceramic substrate, or a polymer substrate, in particular a flexible polymer substrate, for example. However, the substrate may also include one or more layers deposited on a semiconductor substrate, as is achieved, for example, by means of a CMOS process, on which layers the sensitive film finally is arranged. The term substrate is used in connection with a single sensor chip, while a wafer constitutes a common substrate for building multiple sensor chips from.

An area of the substrate is designated to accept the sensitive material for finally forming a sensitive film. In view of the miniaturization of sensor chips, it is desired to minimize the area on/of the substrate covered by the sensitive material. In case of multiple sensor cells the sensitive films of these multiple sensor cells are desired to be arranged close to each other in view of space saving considerations. The area for building the sensitive film may be defined upfront as a dedicated region on the substrate. It is preferred that the/these areas are confined in order to save space on the substrate. Hence, it is preferred to provide an expansion inhibitor which prevents sensitive material to be dispensed to the designated area to escape from this area, or in other words, to expand or to spill over from this area.

The expansion inhibitor may comprise, for example, a barrier for stopping an expansion of the sensitive material by means of blocking a flow of the sensitive material in a direction outside the dedicated area. Such barrier may, for example, include a rim emerging from the substrate which blocks an expansion of the sensitive material. The rim may be added to the substrate, e.g. by photolithographic processing, or may be formed as part of the substrate. While such rim typically denotes a protruding barrier, a recess in the substrate may also act as a barrier given that when the sensitive material meets a falling edge of the recess, surface tensions may prevent the sensitive material from entering the recess.

A barrier may typically be arranged around the area, i.e. arranged at the edges of the area, and preferably encircle the area, and as such confine the area in its lateral extension on the substrate. A basin/s for accepting the sensitive material in a confined area shall be subsumed under the expansion inhibitor, too.

In another embodiment, an adhesion film may be applied to the area of the substrate where the sensitive film is intended to be built. Such adhesion film may act as an expansion inhibitor, and, for example, may contain oxide or nitride, such as silicon oxide, silicon nitride, aluminium oxide, titanium oxide, or tantal oxid. In another embodiment, the adhesion film may contain silane. In a further embodiment, the adhesion film may contain a polymer material, such as polyimide or polyamide. In another step the sensitive material may be applied to the adhesion film and stick thereto without spilling over the edges of the adhesion film. In this and other embodiments, it is preferred to supply only a defined portion of sensitive material to each area which portion may be defined upfront.

In another embodiment, a surface of the substrate is treated/patterned such that the surface in said area provides a first surface energy while a region outside said area—and in case of multiple of said areas for building multiple sensitive films on the region between said areas—provides a second surface energy which second surface energy is less than the first surface energy for making said area a preferred zone for the sensitive material to wet to.

Hence, in this embodiment, the surface of the substrate is patterned as to generate a higher/first surface energy in said area and a lower/second surface energy outside said area. This leads to a preferred wetting of the sensitive material being dispensed to the substrate in a liquid phase to said area of the higher/first surface energy. In case, the liquid phase sensitive material is trying to expand into the surrounding of said area, it will be repelled owed to the lower/second surface energy which is less prone to wetting than the higher/first surface energy in said area. Hence the liquid phase sensitive material will be confined to said area of the first surface energy.

For example, said area may be coated by a hydrophilic coating while the region outside said area is of hydrophobic nature, for example owed to a coating of this nature being applied to this region.

Hence, a property of the surface of the substrate to allow wetting by the sensitive material solution is different between said area and the region outside said area, and specifically the region immediately around said area.

In one embodiment, the surface of the substrate may in said area may be treated by means of e.g. plasma structuring. The surface of the substrate to be treated in such way preferably is an oxide or nitride layer of the substrate. For chemically structuring the subject areas, silane, may be applied to such area in one embodiment, and specifically hexamethyldisilazan or octyltrichlorsilan.

While the above embodiment may be generalized by first providing a substrate surface containing the second surface energy all over the substrate, e.g. by providing a coating containing such second surface energy, and subsequently applying a coating containing the first surface energy in said area/s or otherwise treating said area/s to exhibit the first surface energy, in an alternate embodiment a substrate surface may be provided containing the first surface energy all over the substrate, e.g. by providing a coating containing such first surface energy, and subsequently a coating containing the second surface energy may be applied to a region outside.

By means of such surface energy treatment the liquid phase material is confined to said area/s and may dry in said desired locations.

In another embodiment, the expansion inhibitor may be an electrode pattern arranged on the substrate. Such electrode pattern may represent a modification to the surface of the substrate that impacts an expansion of the liquid sensitive material dispensed to the surface of the substrate. Preferably, the electrode pattern provides electrode sections essentially confining the area for the sensitive material. Hence, it is preferred, that the electrode pattern represents a structure with an outer boundary of essentially square, circle or other shape with or without further electrode sections residing inside this boundary such that when dispensing the sensitive material onto the electrode pattern its expansion may be prevented by means of the electrode pattern. Such electrode pattern on the one hand may constitute a slight protrusion similar to the protruding rim, and on the other hand may have surface tension impact on the sensitive material.

It is preferred that such electrode pattern is made from one of gold, platinum and aluminum. It is preferred, that an electrode of such electrode pattern has a height between 40 and 250 nm. It is preferred that the electrode pattern is applied to an oxide or nitride layer of the substrate, e.g. a silicon oxide, silicon nitride or aluminium oxide layer. A surface of the electrode pattern and/or a surface of an area between electrodes of the electrode pattern may be chemically treated for adjusting a surface energy as was introduced before. A preferred means for such treatment of the surface of the electrode pattern is based on thiol chemistry. A preferred means for such treatment of the surface of the area between the electrodes is based on silane chemistry.

In addition, the electrode pattern may be used for contacting the sensitive film and "reading" information as to the presence and/or concentration of a chemical analyte interacting with the sensitive film.

When the sensitive material is dispensed to the assigned area, it is preferably dispensed in a contactless way. This means that there is no contact between a dispenser of the sensitive material and the substrate. Hence, a gap between the dispenser and the substrate has to be overcome by the sensitive material. In contrast, contact printing would be understood as pressing the dispenser against the substrate, such that for example a stamp covered by ink acting as dispenser is brought into contact with the substrate for transferring the ink to the substrate. There is no gap to be overcome by the ink in contact printing.

For implementing a contactless dispensing, it is preferred to provide the sensitive material as a liquid, e.g. in a container, and dispense the sensitive material in liquid form to the substrate on the designated areas.

Contactless dispensing may preferably include jet dispensing wherein a continuous jet of liquid or discrete jet of liquid—e.g. in form of individual drops—is applied under pressure, e.g. by using a tight nozzle, to the substrate. Hence, jet printing may include an acceleration of the liquid in the dispenser to form a jet.

Preferably, the sensitive material is dispensed to the substrate in liquid phase, i.e. in a liquid state.

Hence, the jet dispensing approach may result in the sensitive material meet the substrate at high impact. This may be one of the reasons, why it is desired to provide an expansion inhibitor for confining the impacting jet to the designated area. However, even after having dispensed the sensitive material to the substrate the sensitive material may at least for a limited period in time be flowable on the substrate and may want to escape the designated area in order to reach its state of lowest energy. This is another instance when the expansion inhibitor prevents from such undesired escape of the sensitive material from the designated area. In a beneficial secondary effect, even after a solvent may be evaporated from the sensitive film, e.g. by heating the substrate, and after the sensitive material is dried, e.g. by sintering, tempering, etc., and becomes a more or less solid sensitive film, the expansion inhibitor may support fixing the sensitive film in its position on the designated area.

In a preferred embodiment, the sensitive material includes nano-particles in a suspension or solution, for example metal oxide nano-particles, which suspension or solution is dispensed to the substrate.

In another preferred embodiment, the sensitive material includes polymer material, especially a soluble polymer material, such as polyimide, polythiophene, polyurethane, or polyaniline.

In the context of printing the sensitive material, the sensitive material may also be denoted as ink. An ink reservoir of a print head may be filled with the suspension, and the suspension may be jet printed onto the area on the substrate for depositing the sensitive material there.

Specifically, the underlying ink jet printing technology may be one of the following:

In continuous ink jet printing a high pressure pump directs the liquid ink from a reservoir through a gunbody and a microscopic nozzle, thereby creating a continuous stream of ink droplets via the Plateau-Rayleigh instability. A piezoelectric crystal creates an acoustic wave as it vibrates within the gunbody and causes the stream of liquid to break into droplets at regular intervals. The ink droplets are subjected to an electrostatic field created by a charging electrode as they form; the field varies according to the degree of drop deflection desired. This results in a controlled, variable electrostatic charge on each droplet. Charged droplets are separated by one or more uncharged "guard droplets" to minimize electrostatic repulsion between neighbouring droplets. The charged droplets pass through an electrostatic field and are deflected by electrostatic deflection plates to print on the destination.

In thermal ink jet printing, print cartridges with a series of tiny chambers each containing a heater, are used to eject a droplet from each chamber, by applying a pulse of current to the heater thereby causing a rapid vaporisation of the ink in the chamber to form a bubble, which causes a large pressure increase, and propels a droplet of ink onto the destination. The ink's surface tension, as well as the condensation and thus contraction of the vapour bubble, pulls a further charge of ink into the chamber through a narrow channel attached to an ink reservoir.

In piezo ink jet printing, a piezoelectric material is arranged in an ink filled chamber behind each nozzle instead of a heating element. When a voltage is applied, the piezoelectric material changes shape, which generates a pressure pulse in the fluid forcing a droplet of ink from the nozzle.

However, in other embodiments, the contactless dispensing of sensitive material shall include one of screen printing, spraying, and jet dispensing.

The sensitive film may be printed not only in one process step but may instead be printed in multiple steps for forming multiple layers of sensitive material upon each other which collectively form the sensitive film.

By means of contactless printing the sensitive material to the substrate an integrated chemical sensor array—also denoted in some instances as a gas sensor array—may be manufactured in which the sensitive material is additively deposited, i.e. the sensitive material is only deposited where needed. Patterning and deposition/dispensing are preferably done in the same processing step. Deposition/patterning of different materials may be achieved at the same time when using a sensitive material of different composition for building multiple sensitive films of a sensor array. In case of a print head used, the chambers/containers/reservoirs of the print head may be loaded with different inks. In such embodiment, it is preferred to provide a print head with many different nozzles, wherein each nozzle is assigned to the sensitive material of a specific composition. Typically, each nozzle is connected to a dedicated reservoir for holding the particular composition. In such embodiment, and provided that the nozzles are directed at different areas on the substrate, it is possible to simultaneously ink jet print multiple different sensitive films, i.e. different in composition, by using a multi-reservoir, multi-nozzle print head.

In a further embodiment, the sensor cells are monolithically integrated into a common sensor chip with a common substrate for all sensor cells. Such monolithic sensor chip may be encapsulated and be arranged on and electrically connected to a conductor board.

Such chemical sensor chip may, due to its small size, be used in any portable electronic device such as a mobile phone, and in particular a smart phone, a handheld computer, an electronic reader, a tablet computer, a game controller, a pointing device, a photo or a video camera, or a computer peripheral, which listing is not limited, and may support the chemical and/or odour and/or gas identification as to its environment.

FIG. 1 illustrates a top view on a schematic sensor chip 4 according to an embodiment of the present invention. A substrate 5 carries a chemical sensor 1 with multiple sensor cells 11, a humidity sensor 2, and integrated electronic circuitry 3, for example for evaluating sensor signals provided by the chemical sensor 1 and possible the humidity sensor 2.

Preferably, the integrated electronic circuitry 3 is formed by applying a CMOS process while the chemical sensor 1 may, for example, be integrated by applying a MEMS process. Each sensor cell 11 of the chemical sensor 1 is designed for detecting an analyte in a gas supplied. The number of thirty-six sensor cells 11 is only representative.

Figure 2:
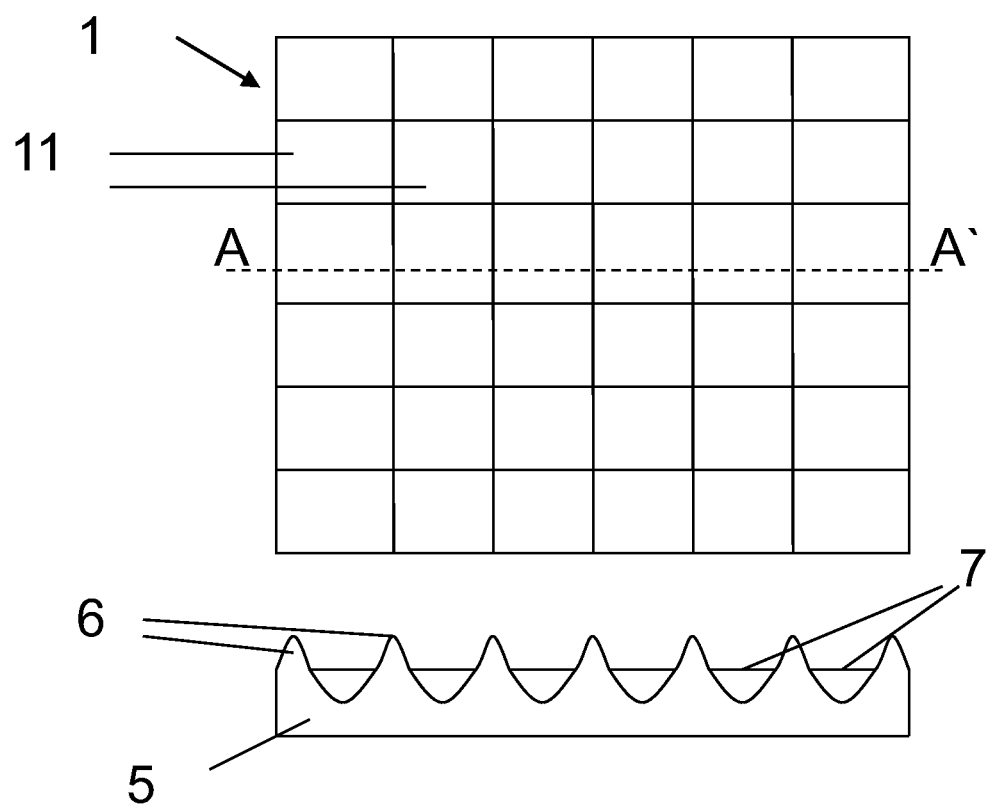

FIG. 2 illustrates a top view on the chemical sensor 1 of FIG. 1, and a cut along lines A-A' at its bottom. The substrate 5 contains barriers 6 in form of elevations/protrusions from the substrate 5. Between the barriers 6, the sensitive films 7 are built in basins of the substrate 5. Those sensitive films 7 are built by jet dispensing of sensitive material to the designated areas between the barriers. In the top view, the sensor cells 11 are schematically represented by adjacent rectangle areas, while from the cut view it is apparent that the sensitive films 7 cover a smaller area on the substrate 5 given that the barriers 6 claim some space on the substrate 5, too. While the barriers 6 may in one embodiment be formed by etching the substrate 5 in the designated areas resulting in the barriers 6 be formed by the substrate 5 itself, in another embodiment, the barriers 6 may be separately grown on or be attached to the substrate 5 such as by photolithographic processes, etc.

Figure 3:
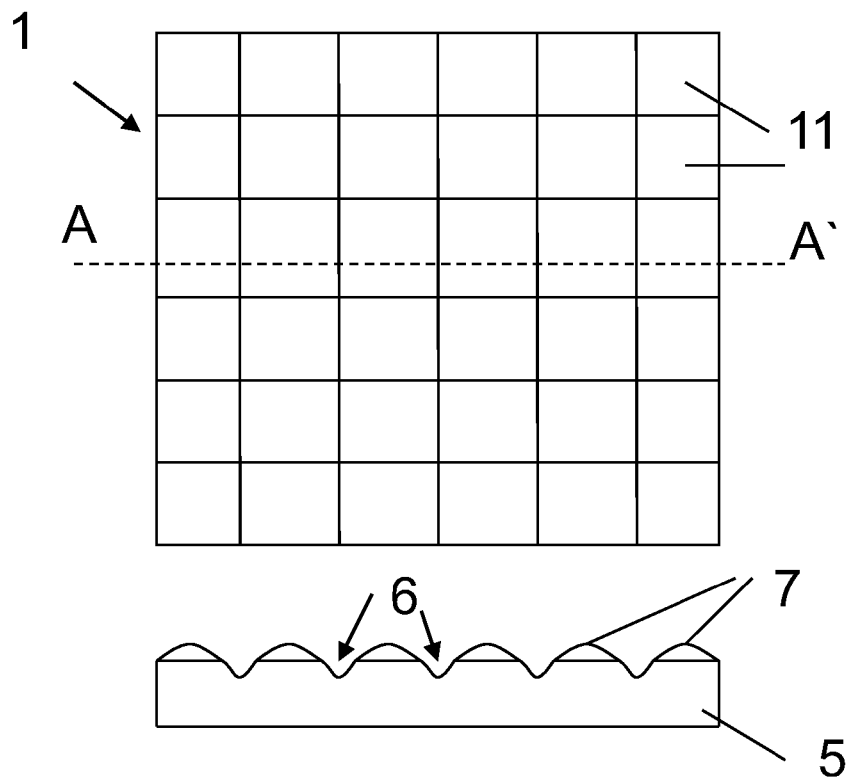

FIG. 3 illustrates a top view on another chemical sensor 1 according to an embodiment of the present invention. In contrast to the sensor of the embodiment of FIG. 2, the barriers 6 are now embodied as recesses in the substrate 5, while the sensitive films 7 are built on the non-recess areas of the substrate 5. Such embodiment makes use of surface tensions in the sensitive material when being applied in liquid form to the substrate 5. Such surface tensions evoked by falling edges of the recesses support the sensitive material retaining at the designated areas instead of flowing into the recesses.

Generally, an expansion inhibitor may encircle the designated area at its edges. There may be provided an individual expansion inhibitor for each sensor cell 11, e.g. there may be an individual rim provided around each sensor cell 11. In another embodiment, two adjacent sensor cells 11 may comprise a common part in their expansion inhibitors, such as, for example a single wall or a single recess between the corresponding adjacent areas. Hence, the barriers 6 may form a grid between the areas reserved for dispensing the sensitive material to.

Figure 4:
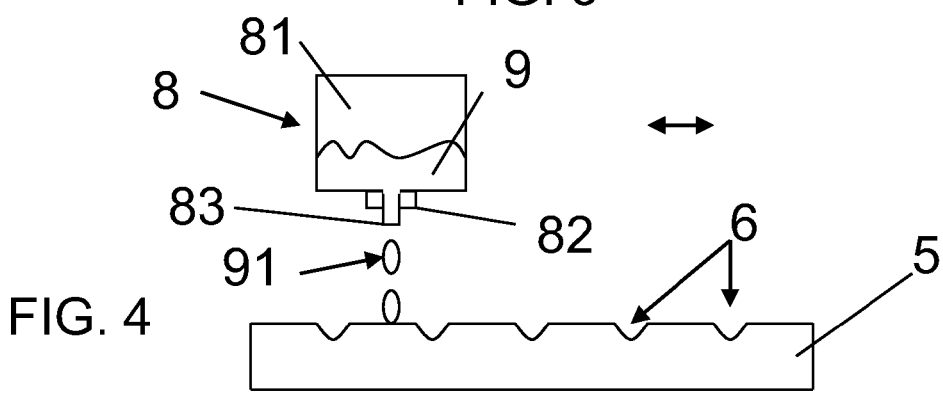

FIG. 4 shows a schematic cut illustrating the manufacturing of a chemical sensor according to an embodiment of the present invention. A substrate 5 is provided with recesses acting as barriers 6. Hence, the expansion inhibitors are already implemented. Now, the sensitive material 9 will be applied to the designated areas on the substrate for finally building a chemical sensor according to FIG. 3. For this purpose, a print head 8 is provided comprising a container 81 holding the liquid sensitive material 9. The print head 8 comprises a piezo actuator 82 arranged at a nozzle 83 of the print head 8 for forming and ejecting droplets 91 of the sensitive material 9 towards the substrate 5. The arrow may indicate a motion direction of the print head such that in one embodiment, after having finalized dispensing the sensitive material 9 to the present area between two barriers 6, the print head 8 may move on to the adjacent designated area, and the piezo actuator 82 of the print head 8 is controlled as to eject droplets 91 to said adjacent area.

Figure 5:
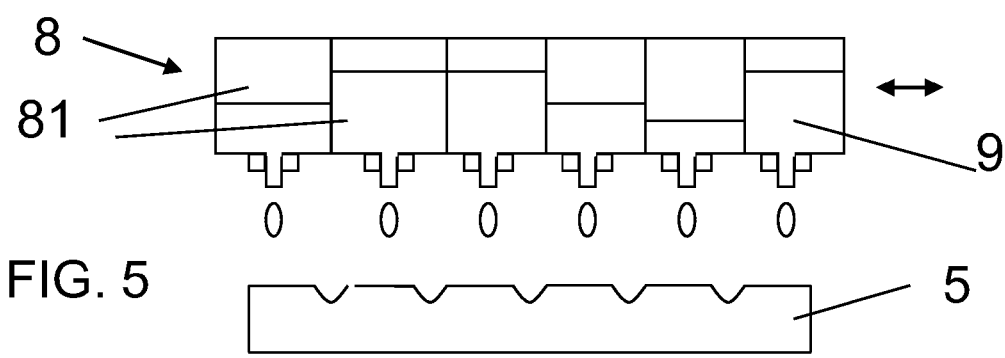

In another embodiment according to FIG. 5, the very same substrate 5 now is ink jet printed by means of a different print head 8 comprising multiple containers 81 for holding the sensitive material 9. Each container 81 is assigned an individual nozzle 83 and an individual piezo actuator 82, such that when controlling the piezo actuators 82 properly, in this example six areas in a row may be printed simultaneously with the sensitive material 9. In case each container 81 holds sensitive material 9 of a different composition sensitive films of different material may be built next to each other on the substrate 5 with a gap in between owed to the expansion inhibitors. The print head 8 may be a one-dimensional print head with several individual subunits next to each other such as shown in FIG. 5. In another embodiment, the print head 8 may be a two dimensional print head with individual subunits next to each other in two dimensions forming a planar print head for printing sensitive material in two dimensions on the substrate 5. It this embodiment, it is preferred that at least nozzles of the print head are arranged next to each other at about a distance that corresponds to a distance between two cells such that during printing each nozzle is arranged above the area assigned to printing a sensor cell to. In case the number of subunits corresponds to the number of areas for building sensitive films on the sensitive material can be dispensed to all areas simultaneously.

Figure 6:
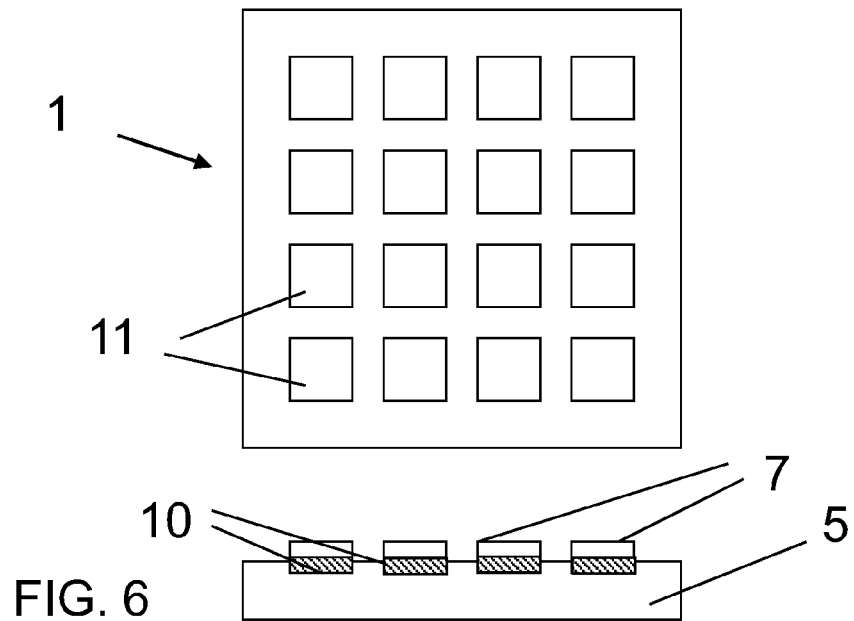

FIG. 6 illustrates a top view on another chemical sensor according to an embodiment of the present invention, including a cut along lines A-A'. From the side cut, it can be seen that surface areas 10 corresponding to said areas for building the sensitive films 7 on are pretreated in that the surface energy in said areas is improved for the liquid phase sensitive material to wet to.

Figure 9:
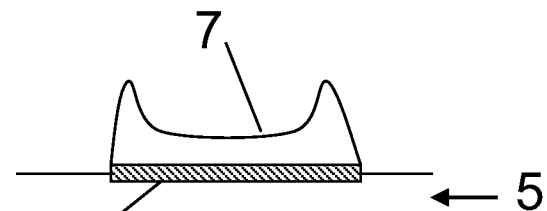

A more detailed and less schematic view of a single sensor cell in depicted in FIG. 9 in a cut. It can be derived that the sensitive film 7 builds on said area and is confined to it by means of a surface energy in said area exceeding the surface energy of a region around said area.

For both embodiments of FIG. 6 and FIG. 9, in an alternate approach, the region around said area/s 10 may be pretreated such that the surface energy in this region is/becomes less than the surface energy in said area for depositing the sensitive film. For example, a coating of the second surface energy is applied to such region outside said area in case the substrate as such is of a first surface energy exceeding the second surface energy. In one example, the surface of the substrate 5 is an oxide or nitride surface which is treated in the region/s outside said areas as to make the surface energy in said regions become less than the surface energy in said areas which may be the surface energy inherent in the substrate. Silane, for example, may be applied as a coating to such regions, and specifically one of hexamethyldisilazan and octyltrichlorsilan, for reducing a surface energy of the oxide or nitride surfaces in such regions. After treating/patterning the surface of the substrate 5 in said regions outside said areas 10 in such way, the sensitive material then is printed in form of a solution in contactless manner to said surface areas 10.

Figure 7:
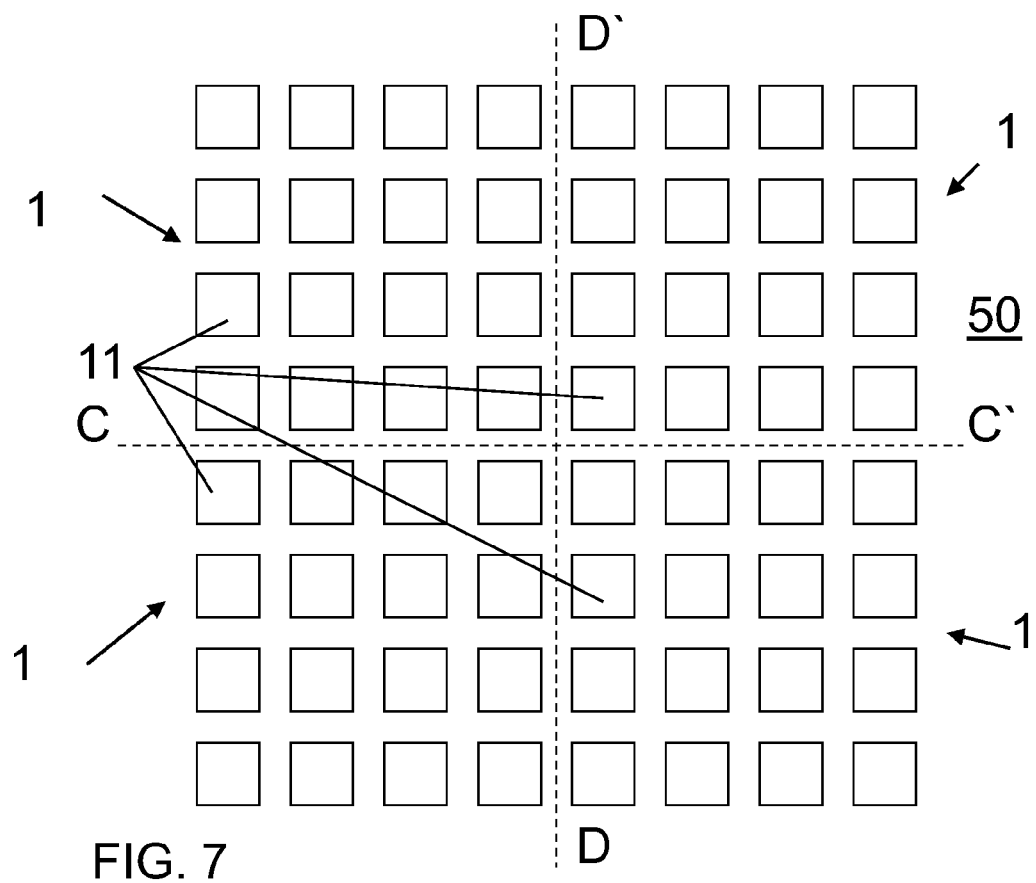

FIG. 7 illustrates a top view on a section of a wafer 50 which contains multiple chemical sensors 1 corresponding to the chemical sensor of FIG. 6. After having applied the adhesion films for all chemical sensors 1 to the wafer 50 in a common step, and after having applied the sensitive material to the expansion inhibitors, possible in a common step, too, the wafer is separated, e.g. by sawing, into the individual chemical sensors 1.

Figure 8:
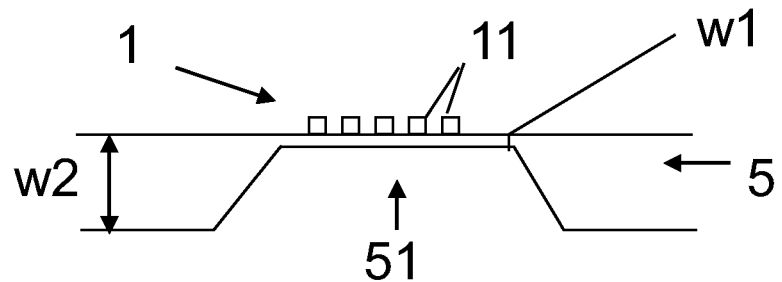

FIG. 8 shows a cut of the chemical sensor section of the sensor chip of FIG. 1. The substrate 5 has a first thickness $w1$ in a first region and a second thickness $w2$ in a second region. The second thickness $w2$ represents a standard thickness of the substrate 5. In the first region where the sensor cells 11 reside, the substrate 5 is thinned to the first thickness $w1$. In case that the sensor cells 11 may include metal oxide sensitive films, such metal oxide sensitive films may be heated prior to taking a reading. In view of an improved heat efficiency, the sensor cells 11 may be arranged in the first region of the substrate 5 with the smaller thickness w1. The first region with the small thickness w1 may be formed by forming a recess 51 into the backside of the substrate 5.

Figure 10:
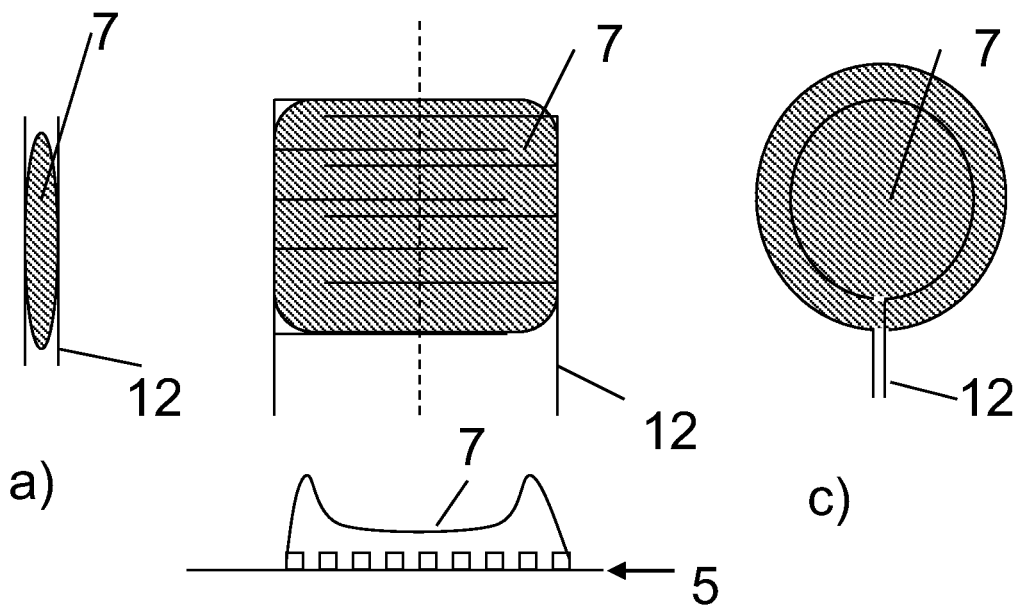

FIG. 10 illustrates a top view on three different designs of a sensor cell of another chemical sensor, wherein an electrode pattern is used as expansion inhibitor. In FIG. 10*a*) the electrode pattern 12 includes two straight electrodes parallel to each other. The two straight electrodes confine the area for the sensitive material such that if the sensitive material is dispensed, e.g. in form or drops, between the two electrodes, its expansion will be confined by these electrodes and a corresponding sensitive film 7 is built. In FIG. 10*b*) the electrode pattern 12 includes two interdigitated electrodes wherein the outermost fingers as well as the connector portions between the fingers on each side define a square within which the sensitive material may expand but outside which the sensitive material is prevented from expansion. Hence, when the sensitive material is dispensed, e.g. in form or drops, on the electrode pattern 12 between its outer boundaries, its expansion will be confined by means of the electrode pattern 12 and a corresponding sensitive film 7 is built. In FIG. 10*c*) the electrode pattern 12 includes two electrodes in form of circles. The outer circle electrode confines the area for the sensitive material such that if the sensitive material is dispensed, e.g. in form of drops, within the outer circle electrode, its expansion will be confined by this electrode pattern 12 and a corresponding sensitive film 7 is built.

For all embodiments of the chemical sensor, electronic circuitry may preferably be integrated in the the subject substrate, specifically by using CMOS processes. Such electronic circuitry may include linearizing, compensating, evaluating, digitizing and/or other functionality.

While there are shown and described presently preferred embodiments of the invention, it is to be distinctly understood that the invention is not limited thereto but may be otherwise variously embodied and practiced within the scope of the following claims.

The invention claimed is:

1. Method for manufacturing a chemical sensor with multiple sensor cells, comprising the steps of
providing a substrate,
applying an expansion inhibitor to the substrate for preventing a sensitive material to be applied to an area on the substrate for building a sensitive film of a sensor cell to expand from said area,
providing the sensitive material, and
building the sensitive film by contactless dispensing the sensitive material to said area,
wherein applying the expansion inhibitor includes treating a surface of the substrate for providing a first surface energy in said area, and for providing a second surface energy outside said area, which second surface energy is less than the first surface energy for making said area a preferred zone for the sensitive material to wet to.

2. Method according to claim 1, wherein applying the expansion inhibitor includes applying a barrier at edges of said area for preventing the sensitive material to be applied to said area to escape from said area.

3. Method according to claim 2, herein the barrier includes a rim protruding from the substrate around said area.

4. Method according to claim 2, wherein the barrier includes a recess in the substrate around said area.

5. Method according to claim 1,
wherein the surface of the substrate provides the first surface energy, and
wherein outside said area the surface of the substrate is covered by a coating providing the second surface energy.

6. Method according to claim 1,
wherein the surface of the substrate provides the second surface energy, and
wherein in said area the surface of the substrate is covered by a coating providing the first surface energy.

7. Method according to claim 1, wherein applying the expansion inhibitor includes applying an adhesion film to said area for making the sensitive material to be applied to said area adhere to the adhesion film.

8. Method according to claim 1,
wherein expansion inhibitors are applied to the substrate for preventing the sensitive material to be applied to multiple areas on the substrate for building sensitive films of the multiple sensor cells to expand from said multiple areas, and
wherein the sensitive films are built by contactless dispensing of the sensitive material to said multiple areas.

9. Method according to claim 1,
wherein the sensitive material is jet dispensed to said area on the substrate, and
in particular wherein a defined portion of the sensitive material is jet dispensed to said area on the substrate.

10. Method according to claim 9, wherein the sensitive material is ink jet printed to said area on the substrate.

11. Method according to claim 10, wherein the sensitive material is ink jet printed to multiple areas on the substrate simultaneously, and preferably is ink jet printed to all areas on the substrate simultaneously.

12. Method according to claim 11, wherein the sensitive material is ink jet printed to said multiple areas on the substrate simultaneously through multiple nozzles of a print head.

13. Method according to claim 10, wherein the sensitive material is applied to a first of said multiple areas in a first composition through a first nozzle of a print head, and is applied to a second of said multiple areas in a second composition through a second nozzle of the print head.

14. Method of claim 13, wherein the sensitive material in the first composition and the sensitive material in the second composition are applied simultaneously through the first and the second nozzle respectively.

15. Method according to claim 1, wherein the sensitive material comprises metal oxide nano-particles.

16. Method according to claim 1, wherein the sensitize material comprises polymer material.

17. Method according to claim 1, wherein the sensitive material is dispensed in a liquid phase to said area.

18. Method according to claim 1, wherein applying the expansion inhibitor includes applying an electrode pattern to the substrate, and in particular includes applying an electrode pattern to the substrate that confines said area.

19. Method according to claim 1, wherein the chemical sensor is a chemoresistive sensor containing a metal-oxide semiconductor material.

20. Method according to claim 1,
wherein the substrate has a first thickness in a first region and a second thickness in a second region wherein the first thickness is smaller than the second thickness,
wherein said area is arranged in the first region such that said sensitive material is dispensed in said first region.

21. Method for manufacturing multiple chemical sensors with multiple sensor cells each, comprising the steps of providing a wafer,
applying expansion inhibitors to the wafer for preventing a sensitive material to be applied to multiple areas on the wafer for building sensitive films of the multiple sensor cells for the chemical sensors to expand from said multiple areas,
providing the sensitive material,
building the sensitive films by contactless dispensing the sensitive material to said multiple areas, and
separating the wafer into the chemical sensors,
wherein applying the expansion inhibitors includes treating a surface of the substrate fir providing a first surface energy in said areas, and for providing a second surface energy outside said areas, which second surface energy is less than the first surface energy for making said areas preferred zones for the sensitive material to wet to.

* * * * *